United States Patent
Mastrotto et al.

(10) Patent No.: US 12,422,372 B2
(45) Date of Patent: Sep. 23, 2025

(54) INSPECTING MACHINE FOR LEATHER AND INSPECTION METHOD APPLICABLE TO SAID MACHINE

(71) Applicant: Brevetti CEA SpA, Sovizzo (IT)

(72) Inventors: Roberto Mastrotto, Sovizzo (IT); Michele Zanin, Sovizzo (IT)

( * ) Notice: Subject to any disclaimer, the term of this patent is extended or adjusted under 35 U.S.C. 154(b) by 454 days.

(21) Appl. No.: 18/044,129

(22) PCT Filed: Aug. 30, 2021

(86) PCT No.: PCT/IB2021/057910
§ 371 (c)(1),
(2) Date: Mar. 6, 2023

(87) PCT Pub. No.: WO2022/053906
PCT Pub. Date: Mar. 17, 2022

(65) Prior Publication Data
US 2023/0333026 A1 Oct. 19, 2023

(30) Foreign Application Priority Data
Sep. 10, 2020 (IT) .................. 102020000021502

(51) Int. Cl.
*C14B 17/00* (2006.01)
*G01N 21/88* (2006.01)
(Continued)

(52) U.S. Cl.
CPC ....... *G01N 21/8851* (2013.01); *C14B 17/005* (2013.01); *G06T 7/0004* (2013.01);
(Continued)

(58) Field of Classification Search
CPC ............ G01N 21/8851; G01N 33/447; G01N 2021/8887; G01N 2201/103;
(Continued)

(56) References Cited

U.S. PATENT DOCUMENTS 7,440,145 B2 * 10/2008 Kuwabara .............. H04N 1/193
358/1.18
2004/0095613 A1 * 5/2004 Kuwabara ............ H04N 1/1903
358/1.18
(Continued)

FOREIGN PATENT DOCUMENTS

| CN | 208860298 | 5/2019 |
|---|---|---|
| WO | 9729368 | 8/1997 |

(Continued)

*Primary Examiner* — Sheela C Chawan
(74) *Attorney, Agent, or Firm* — Themis Law

(57) ABSTRACT

An inspecting machine for leathers includes a feeding unit for moving a leather along an advancement direction; a sensor unit for capturing images of the leather during movement and having contact image sensors arranged perpendicularly to the advancement direction of the leather; and a processing device for identifying geometrical features of the leather based on an analysis of sensor-provided images. The image sensors are staggered perpendicularly to the advancement direction of the leather so that the respective optical fields have corresponding first sections that are superimposed according to the advancement direction to capture first image portions of a same first portion of the leather at two different moments, and corresponding remaining sections for capturing second image portions of two other different portions of the leather adjacent to the first portions, the processing device combining the images captured by the image sensors based on an analysis of the first image portions.

15 Claims, 10 Drawing Sheets

(51) Int. Cl.
   *G06T 7/00*   (2017.01)
   *G06T 7/60*   (2017.01)
   *G01N 33/44*  (2006.01)

(52) U.S. Cl.
   CPC ........ *G06T 7/60* (2013.01); *G01N 2021/8887* (2013.01); *G01N 33/447* (2013.01); *G01N 2201/103* (2013.01); *G06T 2207/30124* (2013.01)

(58) Field of Classification Search
   CPC ....... C14B 17/005; G06T 7/0004; G06T 7/60; G06T 2207/30124
   USPC ................................................ 382/100, 111
   See application file for complete search history.

(56)                  References Cited

U.S. PATENT DOCUMENTS

| | | | |
|---|---|---|---|
| 2011/0280449 A1* | 11/2011 | Campbell, Jr. | D06H 5/00 |
| | | | 353/121 |
| 2013/0176422 A1* | 7/2013 | Campbell | G06V 10/243 |
| | | | 348/95 |
| 2019/0360992 A1 | 11/2019 | Lee | |

FOREIGN PATENT DOCUMENTS

| | | | | |
|---|---|---|---|---|
| WO | 2011030360 | 3/2011 | | |
| WO | WO-2011030360 A1 * | 3/2011 | ............... | C14B 1/00 |
| WO | 2016006007 | 1/2016 | | |

* cited by examiner

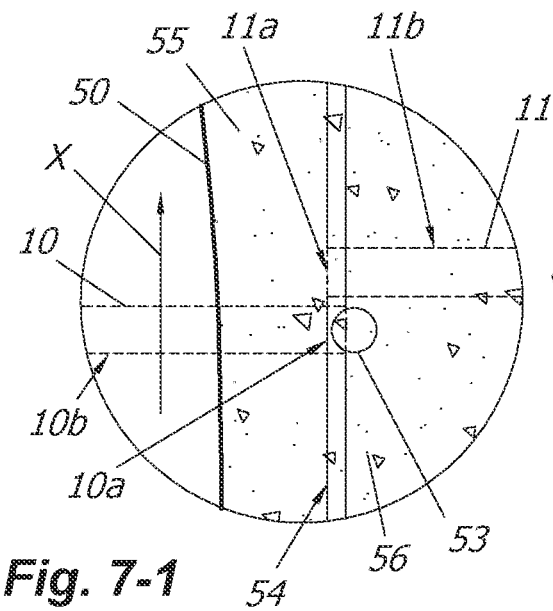
Fig. 7-1
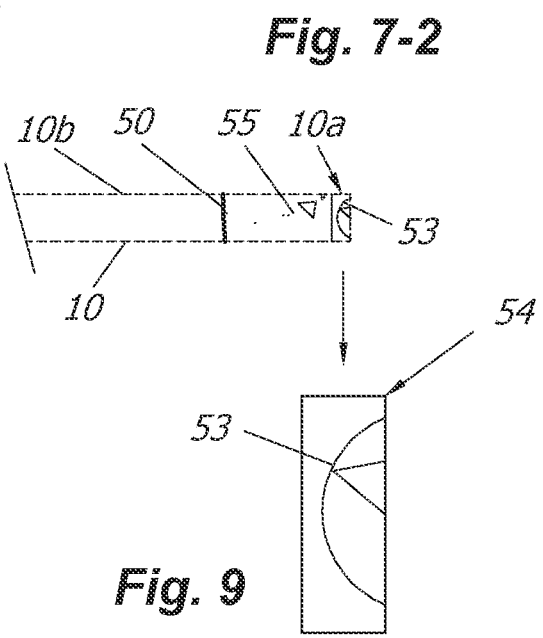
Fig. 7-2
Fig. 9
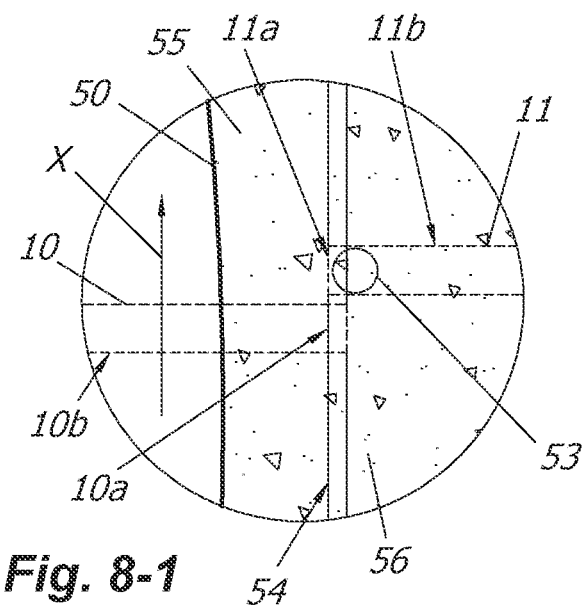
Fig. 8-1
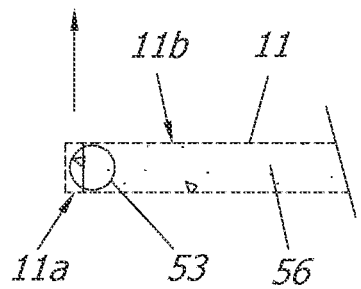
Fig. 8-2

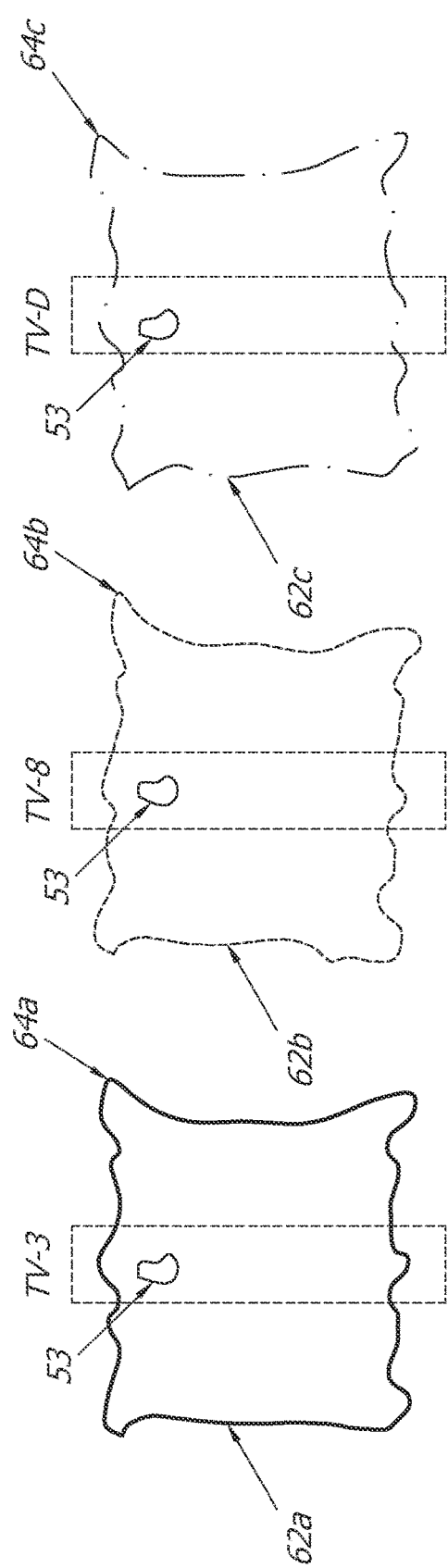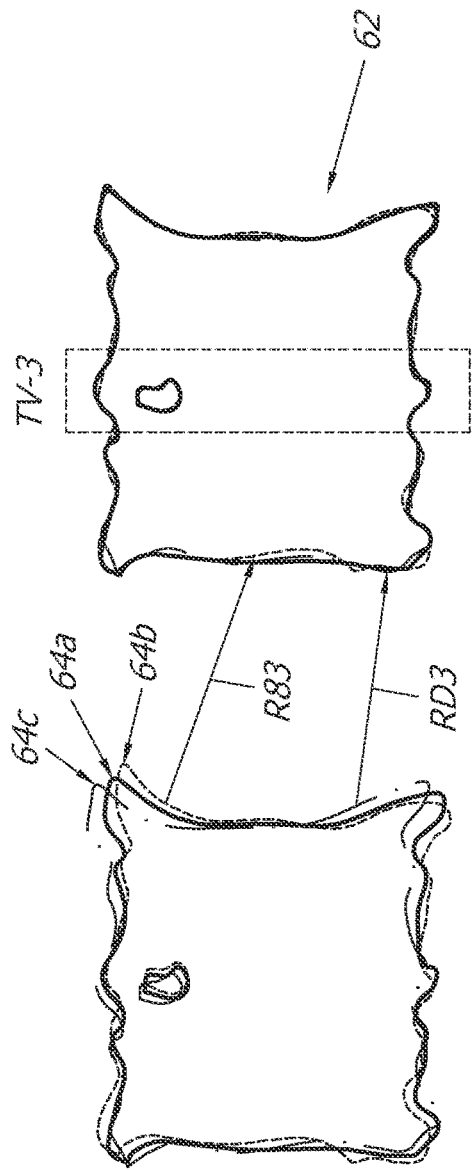

INSPECTING MACHINE FOR LEATHER AND INSPECTION METHOD APPLICABLE TO SAID MACHINE

FIELD OF APPLICATION

The present invention is generally applicable to the technical field of the processing of leathers. In particular, the invention has as its aim an inspecting machine for leathers suited to detect geometrical features of a leather, in particular its defects, as well as an inspection method applicable to the inspecting machine.

STATE OF THE ART

As it is known, leathers must undergo several operations before they can be used for making a finished product. Some of the aforementioned operations are performed during the advance of the leather according to a predefined advancement direction.

Among the aforementioned operations, inspecting operations are also envisaged aimed at detecting the presence of defects on the leather. Known automatic machines for inspecting leathers comprise a feeding device for moving the leather according to an advancement direction, and a vision system based on cameras, that captures images of the surface of the leather during movement. A processor is also present to examine the aforementioned images and, by means of a suitable algorithm, to identify and classify the defects, thus allowing to calculate a parameter that represents the quality of the leather.

An inspecting machine according to a known variant generates a digital map of the leather, containing the coordinate of the observed defects relative to a reference point. The aforementioned digital map can be used in subsequent operations, for example before a cutting operation, to define the usable areas of the leather, in order to optimize the use of the latter and to minimize scraps.

The use of cameras in vision systems of the aforementioned inspecting machines implies some drawbacks. In fact, in order to capture a wide enough area of the leather, the cameras must be arranged relatively far from the surface of the leather. This may bring inaccuracies resulting from vibrations or thermal deformations of the structure that supports the cameras. Moreover, due to the configuration of the camera optics, the image resolution is not uniform in the field of view, but it is higher in the center compared to the periphery. The wider the field of view, the greater the non-uniformity.

The two peculiarities just mentioned bring the drawback to limit the inspection precision that can be achieved, in particular when the leather to be inspected has a big size.

Further drawbacks relate to the known feed devices used to move the leather in the aforementioned inspecting machines.

Typically, a feed device of known kind comprises movable elements to drag the leather by friction. The aforementioned friction is achieved by exerting a compression on the leather by means of counter-rotating roller pairs, pairs of opposite bars, clamps, etcetera.

It is further known that the quality of a leather, hence its commercial value, depends on the surface condition of the leather, that should be as uniform and unaltered as possible compared to its original state.

An element that is decisive for the quality of the leather is its defects, which bring a reduction of the area that can be used to manufacture the finished products.

However, the compression exerted by the above mentioned feed devices of known kind may also alter the leather in the compression points, if not even damage it. The aforementioned alterations imply the drawback of reducing the quality of the leather.

Moreover, the aforementioned feed devices are not able to avoid that the leather slips in the advancement direction. The aforementioned slip may occur for several reasons, among which the slippery of the leather, the unevenness of its surface, the insufficient pressure exerted by the mobile systems on the leather during drag, and so on. The aforementioned slip brings the drawback of reducing the precision of the operations performed by the machine, or even increasing processing scraps, hence the relating costs.

A further drawback of the feed devices of known kind is due to the fact that the length of a leather is limited, and, generally, is comparable to the length of the path through the feed device. As a consequence, the aforementioned feed devices often require the intervention of the operator in order to ensure that the leather is clamped and correctly advanced along the device, so as to prevent formation of wrinkles and unwanted tensions.

Documents WO 2011/030360 A1 and CN 208860298 U disclose inspecting machines for leathers according to the prior art.

PRESENTATION OF THE INVENTION

The present invention aims at overcoming at least in part the above mentioned drawbacks of the prior art.

In particular, it is an aim of the invention to make a leathers inspecting machine allowing to achieve a higher precision of inspection compared to that achievable by the inspecting machines of known kind.

It is also an aim of the invention that the aforementioned inspecting machine allows to perform a precise inspection on leathers of big size as well.

It is also an aim of the invention that the feeding unit does not alter the surface condition of the leather during advance, or, anyway, is such as to induce smaller alterations compared to that induced by the feed devices of known kind.

Another aim of the invention is that the feeding unit be capable to automatically clamp the leather and steadily guide it according to the advancement direction, maintaining a correct tensioning and avoiding formation of wrinkles.

The aforementioned aims are achieved by an inspecting machine according to claim 1.

The aforementioned aims are also achieved by an inspection method according to claim 11.

Further detail features of the invention are specified in the corresponding dependent claims.

Advantageously, the precision of the machine and of the method of the invention allows to reduce the errors in locating the defects, and, consequently, allows a more precise determination of the area of the leather that can be used for the subsequent processing, thus contributing to reduce the processing scraps.

Still advantageously, the higher precision of the machine and of the method of the invention allows to increase the area of the leather that can be used to manufacture the finished products, so as to increase its commercial value.

Still advantageously, the limited alteration of the leather due to the feeding unit allows to preserve the quality of the leather itself.

Moreover, advantageously, the automatic advance of the leather achieved by the feeding unit reduces the intervention by the operator, and, as a consequence, increases the productivity of the feeding unit of the invention compared to the feeding units of known kind.

The aforementioned aims and advantages, together with others that will be mentioned hereinafter, will be clearer from the following disclosure of some preferred embodiments of the invention, that are shown as exemplary and non limiting purpose with the help of the attached drawings.

BRIEF DESCRIPTION OF THE DRAWINGS

FIGS. 7-1 and 8-1 show two respective different moments of the inspection of the leather of FIG. 5.

FIGS. 7-2 and 8-2 show the images captured by the vision system of the inspecting machine of FIG. 1, respectively in the two different moments of FIGS. 6-1 and 7-1.

FIG. 9 shows a portion of the images of FIGS. 7-2 and 8-2.

Figure 10:
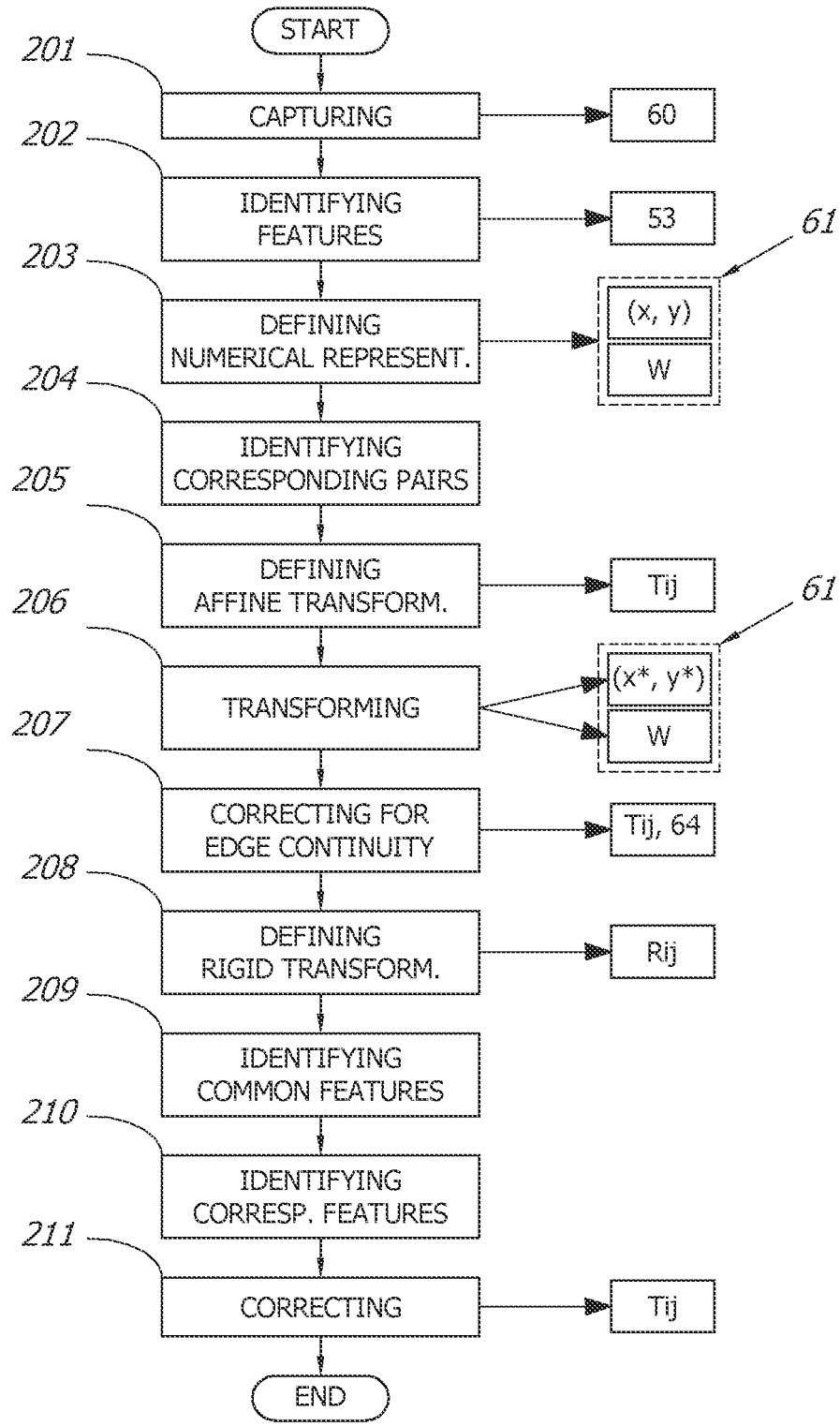
FIG. 10 shows the method of the invention, in diagrammatic view.

FIGS. from 12 to 16 schematically show some steps of the method of FIG. 10.

DETAILED DESCRIPTION OF SOME PREFERRED EXEMPLARY EMBODIMENTS

Figure 1:
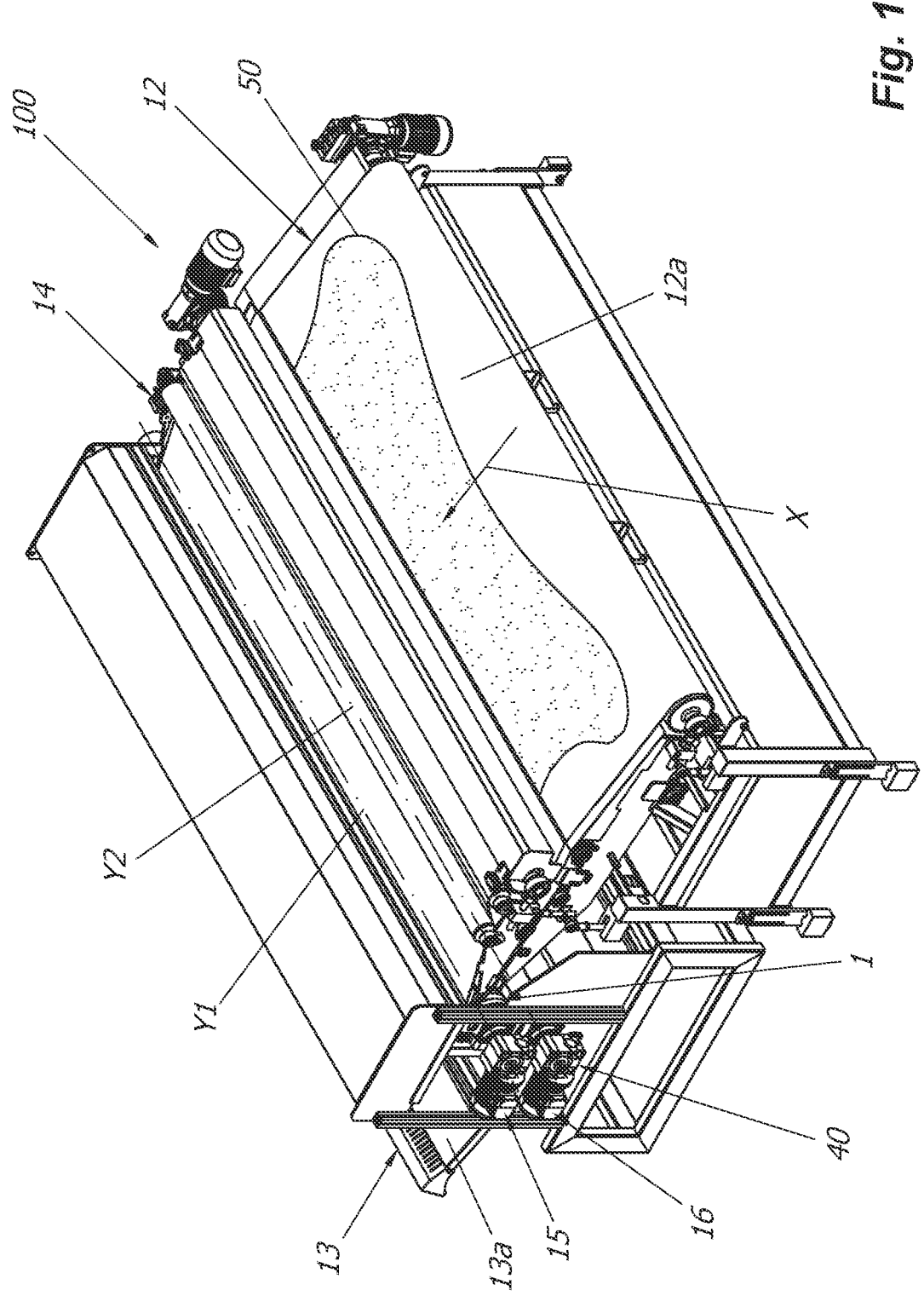
FIG. 1 shows the inspecting machine of the invention, in axonometric view.

The inspecting machine for leathers according the invention, indicated in the overall in FIG. 1 by 100, is configured to detect one or more geometrical features 53 of a leather 50.

The aforementioned geometrical features 53, some of which are schematically shown in the figures from 6 to 9 through corresponding circles, may comprise one or more among: the contour; the defects; other geometrical features present on the surface of the leather but not classifiable as defects, that may be used for example as references for the inspection, as it will be clear in the following.

The inspecting machine 100 comprises a feeding unit 40 configured to make the leather 50 move along the inspecting machine 100 according to an advancement direction X.

It is hereby specified that, in the present disclosure, the term "advancement direction" means a direction along a trajectory, that may be rectilinear, curved, or a combination.

Preferably but not necessarily, the feeding unit 40 comprises an inlet area 12 that receives the leather 50 and conveys it towards the subsequent zone of the feeding unit 40 according to the advancement direction X. Preferably, the aforementioned inlet area 12 comprises a first conveyor belt 12a on which the leather 50 can be automatically or manually arranged.

The feeding unit 40 may receive the leather 50 by another machine arranged upstream, for example along an automatized processing line. In this case, the latter machine may be configured in such a way as to automatically lay down the leather 50 on the inlet belt 12a or, anyway, to convey the leather 50 towards the inlet area 12 of the feeding unit 40.

According to a variant embodiment, the inlet area 12 may be configured to allow to manual load the leather 50 by an operator. This variant is particularly suited for the case in which the feeding unit 40 is not preceded by another machine in a same processing line.

Figure 2:
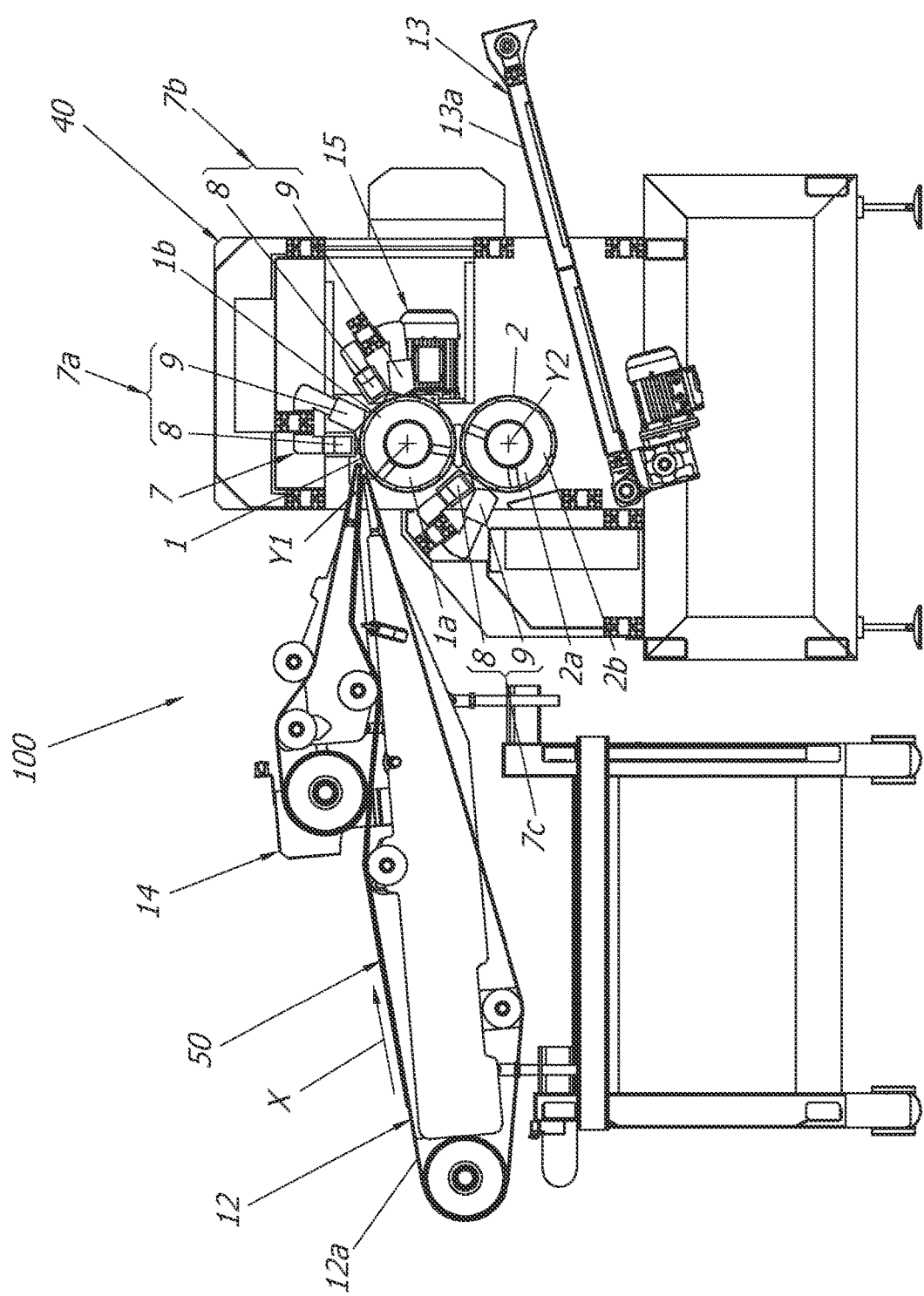
FIG. 2 shows the inspecting machine of FIG. 1, in lateral sectioned view.

Still preferably, and as shown in FIG. 2, the feeding unit 40 comprises a stretching unit 14 configured to stretch the leather 50 while it moves along the inlet area 12, in order to eliminate possible wrinkles.

Preferably but not necessarily, the stretching unit 14 comprises a conveyor belt faced to the inlet belt 12a and kept in tension between corresponding rollers. The stretching of the leather is achieved thanks to an advance speed of the conveyor belt of the stretching unit 14 being higher than that of the inlet belt 12a.

The feeding unit 40 also comprises two feeding rollers 1, 2, that may be seen in FIG. 2, which define corresponding longitudinal axes Y1, Y2 perpendicular to the advancement direction X.

As it will be apparent hereinafter, in variant embodiments of the invention not depicted in the drawings, the number of feeding rollers 1, 2 may differ from two, for example being only one or more than two.

Each feeding roller 1, 2 is rotatably mounted for the rotation according to the corresponding longitudinal axis Y1, Y2, and is delimited by a cylindrical surface in contact to which the leather 50 can be arranged.

Motorization means 15, 16 are further present, which may comprise electric motors and/or any other similar devices in themselves known, for the controlled rotation of each feeding roller 1, 2 according to the corresponding longitudinal axis Y1, Y2 in a corresponding rotation direction Z1, Z2. As a consequence, the cylindrical surface of each roller 1, 2 is a corresponding mobile surface 3, 4 that, as a result of the rotation of the roller itself, is moved according to the advancement direction X.

For clarity reasons, each mobile surface 3, 4 will be referred to in the following by the expression "cylindrical surface", but what will be disclosed is applicable, with the due and obvious changes, to a mobile surface of any kind and shape.

Each one of the cylindrical surfaces 3, 4 of the rollers 1, 2 comprises a corresponding plurality of holes 5. The feeding unit 40 comprises a depression generation device, not shown in the drawings but of a kind in itself known, that can be connected to one or more of the aforementioned holes 5 to generate a depression at the level of each cylindrical surface 3, 4, the depression being suited to keep a respective portion 51, 52 of the leather 50 in contact with the cylindrical surface 3, 4 during the rotation of the corresponding feeding roller 1, 2.

In other words, the depression generation device produces a suction force through the holes 5, with the effect of keeping the portions 51, 52 of the leather 50 in contact to, respectively, the cylindrical surfaces 3 and 4. As a consequence, the leather 50 is set in motion according to the advancement direction X by each feeding roller 1, 2 as a result of the rotation thereof.

It is understood that the aforementioned movement of the leather 50 is achieved without compressing the leather 50, hence reaching the aim of avoiding alterations thereof.

Moreover, the aforementioned suction force may be exerted on a relatively wide portion 51, 52 of the leather 50, in order to limit possible slipping of the leather 50 relative to the feeding rollers 1, 2, with the advantage of achieving a high precision of movement of the leather 50, hence improving the precision of inspection.

According to different embodiments of the feed device 40, not shown in the drawings, each cylindrical surface may be replaced by a corresponding mobile surface 3, 4 of any shape and kind, rigid or deformable, as long as it is provided with holes connected to the depression generation device. A variant embodiment may envisage that each mobile surface belongs to a corresponding conveyor belt, in which case the mobile surface is deformable.

Preferably, the aforementioned depression generation device is a blower or, more generally, any device suited to suck air through the holes 5 in order to generate the aforementioned depression.

Preferably but not necessarily, each feeding roller 1, 2 is a corresponding hollow drum 1a, 2a, whose cavity 1b, 2b is delimited by a cylindrical wall 1c, 2c through which the holes 5 pass. The cavity 1b, 2b is put in communication with the depression generation device, in such a way that the depression thereby generated is transmitted to the holes 5 and, from there, to the cylindrical surfaces 3, 4.

Figure 4:
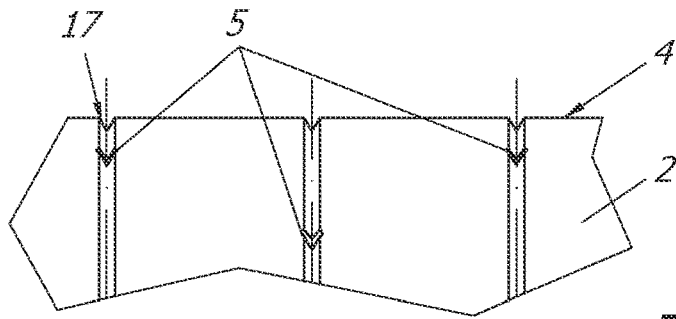
FIG. 4 shows an enlarged detail of the feed device of FIG. 3, in front view.

FIG. 4 shows a detail of the roller 2, in plan view according to a plane parallel to the longitudinal axis Y2 of the roller. Preferably, the holes 5 are aligned in correspondence to a plurality of circumferences, indicated in the figure with dash-dot lines, which are coaxial to the longitudinal axis Y2 of the roller 2 and are spaced along the direction of the axis. Still preferably, the holes 5 are arranged at regular intervals along each circumference, in order to distribute the suction force more uniformly. For the same reason, the holes 5 of each circumference are angularly offset with respect to the holes 5 of the circumferences adjacent thereof, as it may be clearly seen in the figure.

Preferably and as shown again in FIG. 4, the cylindrical surface 4 defines, in correspondence to each of the aforementioned circumferences, a corresponding groove 17 to which the corresponding holes 5 lead. As a consequence, the holes 5 are, in whole or in part, slightly lowered relative to the cylindrical surface 4. This, advantageously, prevents the leather 50 from coming into direct contact with the holes, thus avoiding consequent markings of the surface of the leather. Still advantageously, the depression generated by the holes 5 of a given circumference is being distributed along the corresponding groove, thus generating a suction force that is substantially uniform along the entire portion 52 of the leather 50 that is in contact with the roller 2.

In a variant embodiment of the invention, not shown in the drawings, the aforementioned grooves 17 may have a different configuration than the one just disclosed, as long as the holes 5 lead to the groove. For example, the grooves 17 may be developed according to corresponding straight lines parallel to the longitudinal axis Y2, or they may have a helical pattern around that longitudinal axis.

It is clear that the configurations of the holes 5 and of the grooves 17 just disclosed are applicable as such to the roller 1 as well.

As regards the shape of the holes 5, preferably but not necessarily they have circular section at least at their ends facing towards the cylindrical surface 3, 4.

Figure 3:
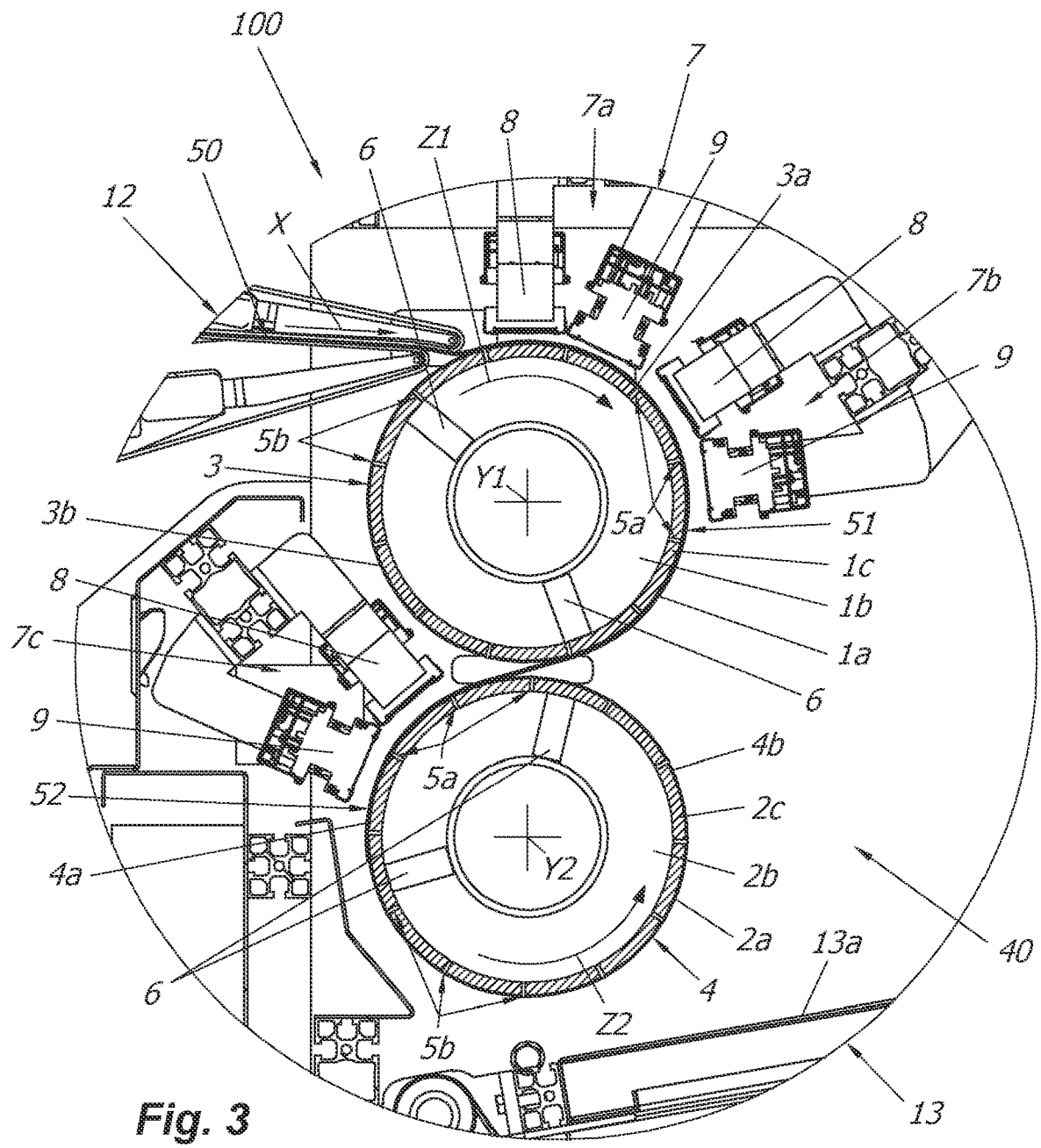
FIG. 3 shows an enlarged detail of FIG. 2, corresponding to the feed device of the inspecting machine.
Figure 5:
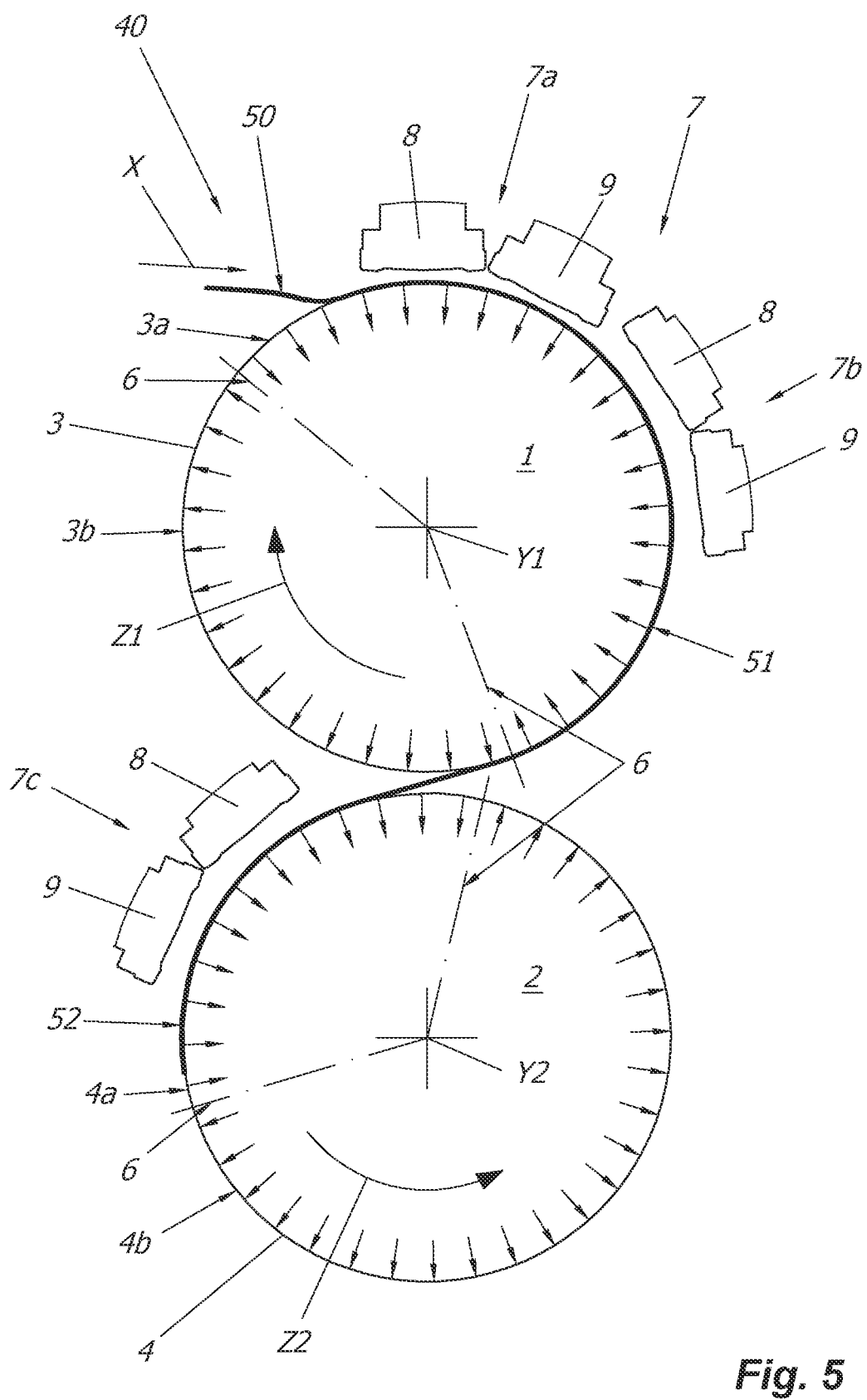
FIG. 5 schematically shows the operation of the feed device of FIG. 3.

Still preferably, and as shown in FIG. 3, the feed device 40 comprises a sealing unit 6 operatively associated to each roller 1, 2 and configured to limit the transmission of the depression generated by the depression generation device only to a first group of holes 5a, 5b that are located within a first area 3a, 4a of the cylindrical surface 3, 4, thus excluding the transmission of the depression to the remaining holes 5. As a consequence, the suction effect on the leather 50 is only limited to the aforementioned first area 3a, 4a. The aforementioned suction effect is schematically indicated in FIG. 5 through the arrows oriented towards the center of each roller 1, 2, while the sealing unit 6 is ideally represented by dash-dot lines, indicating its operating area.

Clearly, if the mobile surfaces are not cylindrical, the aforementioned first area of each mobile surface is to be meant as a portion of the mobile surface developing along a portion of the advancement direction X. The same applies for any other area of the surface that will be defined hereinafter.

The sealing unit 6 can rotate independently of the feeding roller 1, 2, in such a way that the corresponding first area 3a, 4a stay stationary during the rotation of the roller. To that end, the sealing unit 6 is preferably fixed to the structure of the feeding unit 40 on which the rollers 1, 2 are rotatably mounted.

Advantageously, by limiting the suction effect only to the holes 5a, 5b of the first group, the leather 50 is allowed to spontaneously detach from the cylindrical surface 3, 4 so that the leather 50 can be more easily directed towards devices located downstream of the roller 1, 2. Therefore it is achieved the aim of facilitating the movement of the leather 50 according to the advancement direction X, preventing formation of curves and wrinkles that might require the intervention of the operator or prejudice the processing.

Preferably, the feeding unit 40 further comprises a pressure generation device that can be connected to one or more of the holes 5 included in a second area 3b, 4b of the cylindrical surface 3, 4 of one or more of the feeding rollers 1, 2, the second area 3b, 4b being arranged downstream of the first area 3a, 4a according to the advancement direction X, that, in the present embodiment, corresponds to the rotation direction Z1, Z2 of the roller 1, 2. The configuration just disclosed allows to generate, in correspondence of the aforementioned second area 3b, 4b, a thrust suited to force the separation of the leather 50 from the cylindrical surface 3, 4. The aforementioned thrust is schematically indicated in FIG. 5 by arrows that are directed towards the outside of each roller 1, 2.

Advantageously, the aforementioned thrust further facilitates directing the leather 50 towards the devices arranged downstream of the roller 1, 2, hence improves the motion steadiness of the leather along the advancement direction X.

Preferably, the aforementioned pressure generation device is a blower, or any other device suited to convey a flow of pressurized air towards the holes 5 of the second area 3b, 4b.

Still preferably, the second area 3b, 4b has an end adjacent to the first area 3a, 4a and delimited by the aforementioned sealing unit 6.

Still in FIG. 5, it is shown that, firstly, the leather 50 that moves along the advancement direction X enters into contact with the feeding roller 1, from which it comes to be detached after about a half turn around the roller 1 as a result of the pressure generated by the pressure generation device, in such a way that the leather is driven by gravity towards the second roller 2 arranged below the first one, in such a way that is captures the leather 50 so that it happens to be arranged in contact thereof.

After about 120° around the second roller 2, the leather 50 is detached from it as a result of the pressure generated by the pressure generation device in order to be conveyed by gravity towards an outlet area 13 that is arranged downstream of the second roller 2, shown in FIG. 3. The outlet area 13 receives the leather 50 exiting from the feeding unit 40 and renders it available for possible subsequent operations. Preferably, the outlet area 13 comprises a second conveyor belt 13a, arranged below the second roller 2, onto which the leather 50 is laid.

Still preferably, the feeding unit 40 is configured to put the two opposite faces of the leather 50 in contact with, respectively, the two cylindrical surfaces 3, 4 in succession. As a consequence, each one of the two faces of the leather 50 remains exposed while the other one is in contact with the two rollers 1, 2. The configuration just disclosed brings the advantage that the feed device 40 allows to perform the inspection on both faces of the leather 50 while the leather is in good contact with the cylindrical surfaces 3, 4 of the rollers 1, 2, and, hence, is arranged in a predefined configuration.

Preferably, what has been just disclosed is achieved by configuring the motorization means 15, 16 so as to drive the rollers 1, 2 in rotation according to corresponding mutually opposite rotation directions Z1, Z2.

The inspecting machine 100 also comprises a sensor unit 7 configured to capture images of the leather 50 in correspondence of one or more of the aforementioned portions 51, 52 in contact with each feeding roller 1, 2.

According to a variant embodiment of the invention, that is applicable when the rollers 1, 2 are at least two, as in the embodiment shown in the drawings, the sensor unit 7 may be configured to capture images also in correspondence of the portion of the leather 50 included between the aforementioned portions 51, 52.

The inspecting machine 100 also comprises a processing device, not shown in the drawings but in itself known, configured to detect the geometrical features 53 of the leather 50 based on the analysis of the aforementioned images.

It is understood that the inspecting machine 100 above disclosed achieves the aim of allowing a more precise inspection of the leather 50 compared to what is possible by the known techniques, thanks of the higher advance precision allowed by feeding unit 40, implying a reduced uncertainty on the estimation of the position of the leather 50 along the advancement direction X. In particular, the portions 51, 52 are in contact with the rollers 1, 2 and, thus, accurately follow the geometry of the corresponding cylindrical surfaces 3, 4, allowing to achieve a very precise correspondence between the images and the actual surface configuration of the leather. A high precision can be achieved also for images that are captured on the portion of the leather 50 that is intermediate between the aforementioned portions 51, 52. In fact, despite the fact that such intermediate portion is not in contact with the rollers 1, 2, the good contact of the two portions 51, 52 with the rollers 1, 2 allows to estimate also the position of each point of the intermediate portion more precisely compared to what can be achieved by the known techniques.

As regards more specifically the sensor unit 7, preferably it comprises one or more stations 7a, 7b, 7c for each mobile surface 3, 4, namely for each feeding roller 1, 2. In the variant embodiment shown in the figures, two stations 7a, 7b are provided for roller 1, and one station 7c for roller 2. The two stations 7a, 7b are meant to capture the exposed side of the leather 50, also called "grain side", while the station 7c captures the rear side of the leather 50, also called "flesh side".

As shown in FIGS. 3 and 5, each station 7a, 7b, 7c captures the leather 50 from different positions according to the advancement direction X.

The two stations 7a, 7b of the roller 1 have corresponding mutually different light, respectively raking light and diffused light. The aforementioned different lights allow, advantageously, to more precisely define the geometrical features 53. Clearly, variant embodiments of the invention may envisage a different number of stations and/or different features of the same.

In any case, each station 7a, 7b, 7c comprises one or more image sensors 8, 9 of the "contact" kind (CIS—"Contact Image Sensor") to capture corresponding images of the portion 51, 52 of the leather 50 that is arranged in contact with the roller corresponding.

As known, a CIS sensor is an optical sensor provided with a rectangular field of view, mainly developed according to the longitudinal direction of the sensor itself.

Still advantageously, the aforementioned CIS sensors are configured to be located at close range from the object to be captured, with the consequence of limiting possible capturing inaccuracies caused, for example, by vibrations and thermal deformations of the structure supporting the sensors. By way of example, the distance of each CIS sensor from the surface of the leather 50 is preferably comprised between 10 mm and 20 mm and, even more preferably, is about 12 mm.

The optics of the sensors 8, 9 are of the telecentric kind, that, compared to the common optics, has among its advantages, that of not generating distortions in the image, to allow capturing images with a uniform resolution, and to allow making more precise linear measurements.

Therefore, the use of the CIS sensors allows to achieve a higher precision of inspection compared to the inspection machines of known kind, regardless of the kind of feeding unit 40 that is used.

Moreover, preferably, each sensor 8, 9 integrates a light source to, advantageously, provide an optimal lighting of the leather 50.

Figure 6:
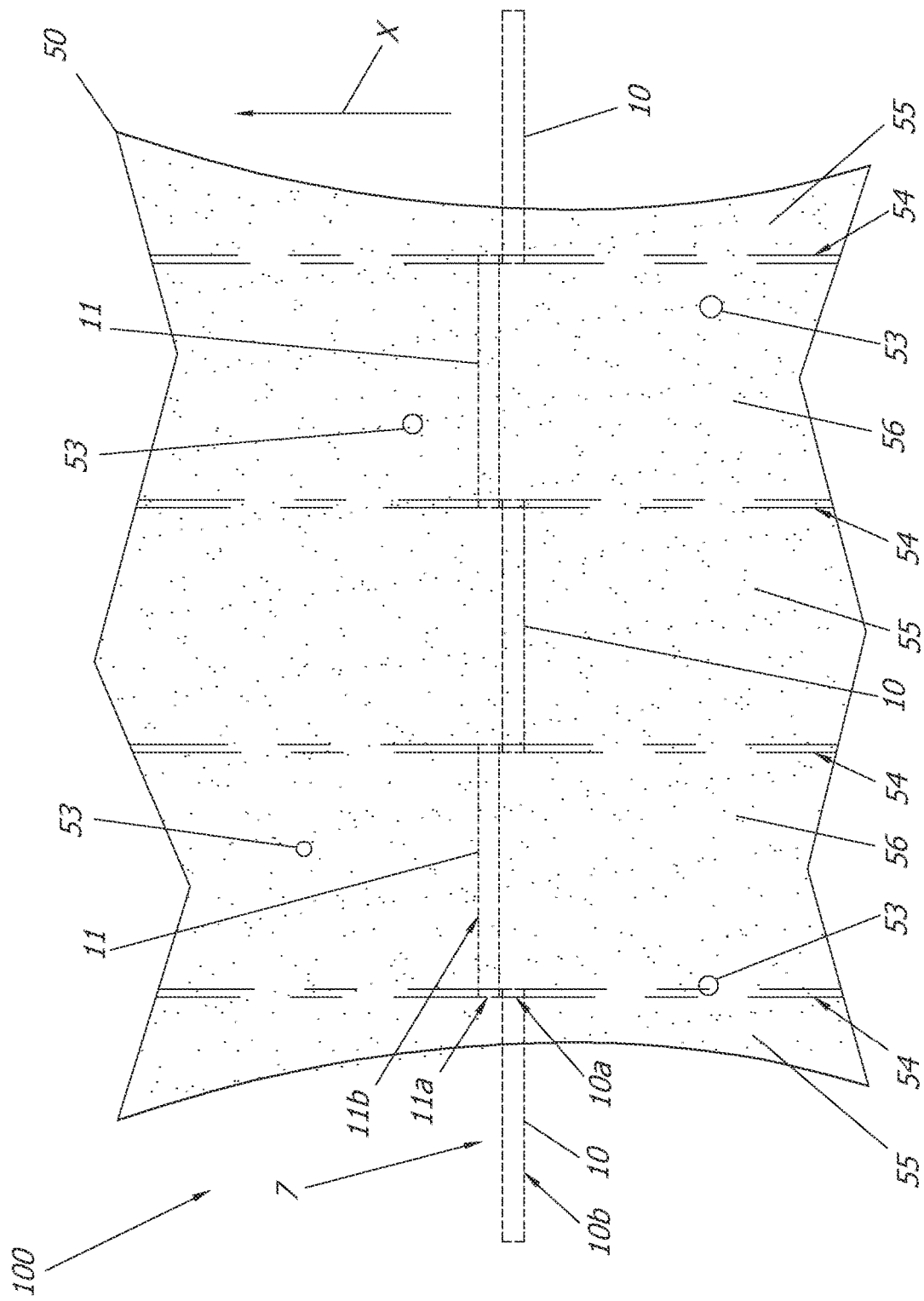
FIG. 6 schematically shows a portion of leather while inspected by the inspecting machine of FIG. 1, in plan view.

The image sensors 8, 9 of each station 7a, 7b, 7c are faced to the corresponding mobile surface 3, 4, so that their longitudinal direction is oriented perpendicular to the advancement direction X that, in the present embodiment, corresponds to an orientation parallel to the longitudinal axis Y1, Y2 of the corresponding roller. Clearly, the fields of view 10, 11 of the sensors 8, 9 are arranged in a similar way, as shown in FIG. 6, representing the fields of view 10, 11 of the sensors of any station 7a, 7b, 7c.

As shown again in FIG. 5, one or more of the stations 7a, 7b, 7c comprises a plurality of the aforementioned image sensors 8, 9, arranged in mutually different positions according to the advancement direction X, in order to capture the leather 50 in corresponding subsequent moments.

In particular, the configuration just disclosed allows to arrange the image sensors 8, 9 of each station 7a, 7b, 7c mutually staggered according to the direction perpendicular to the advancement direction X, namely, in the present case, parallel to the longitudinal axis Y1, Y2 of the corresponding roller.

Advantageously, thanks to the staggered configuration just disclosed it is possible to capture an image of the leather 50 that extends on the entire width thereof. In fact, since the field of view 10, 11 of each sensor 8, 9 of the contact kind does not extend on the entire length of the sensor, but has a length shorter than that of the sensor itself, its ends are blind. Therefore, a position of the sensors 8, 9 in which these are mutually aligned implies that the aforementioned blind ends are interposed between the fields of view 10, 11 of two adjacent sensors 8, 9, hence defining a field of view that, in the overall, comprises intermediate blind zones.

In order to avoid the aforementioned blind zones, the staggering of the sensors 8, 9 is such that the fields of view 10, 11 of each pair of mutually adjacent sensors 8, 9 have corresponding first portions 10a, 11a that are mutually aligned according to the advancement direction X, and remaining second portions 10b, 11b that are not aligned according to the same direction. As a consequence, the aforementioned first portions 10a, 11a are suited to capture corresponding first image portions relating to the same first portion 54 of the leather 50 at two corresponding moments of time, separated by a time interval, while the second portions 10b, 11b capture second image portions relating to other two corresponding mutually different portions 55, 56 of the leather 50 adjacent to the first portion 54, respectively in the aforementioned two moments of time.

The comparison between the aforementioned two first image portions allows the processing device to synchronize the images captured by sensors 8, 9 corresponding to the same roller 1, 2, and to combine them into a single image.

The processing device can synchronize the images through determining the time interval separating the aforementioned two moments of time. To this end, it should be noted that the aforementioned time interval depends on the velocity of the surface of the leather 50 captured by sensors 8, 9. In turn, the aforementioned velocity depends not only on the speed of the feeding rollers 1, 2, but also on other parameters, such as, for example, the elasticity of the leather, that may imply deformations thereof during advancement, or the possible slip of the leather with respect to the rollers 1, 2, as well as on thickness changes of the leather, etcetera.

Therefore, capturing the image of the first portion 54 of the leather 50 by the first portions 10a, 11a in two subsequent moments allows, through an appropriate algorithm, to establish the time interval between the captures by the sensors 8, 9 by making reference to one or more superficial features of the said first portion 54, or it allows to correct the time interval estimated on the basis of the speed of the rollers 1, 2.

What has been just disclosed is shown schematically in FIG. 6, where the fields of view 10, 11 are represented by dashed edges, and the first portions 54 of the leather 50 are indicated by corresponding pairs of dashed lines.

FIGS. 7-1 and 8-1 show a portion of the leather 50 near to the same pair of adjacent sensors 8, 9, respectively in the aforementioned two moments of time. In particular, it may be seen that the leather portion shown in FIGS. 7-1 and 8-1 comprises a geometrical feature 53 of the leather, identified by a corresponding circle.

FIGS. 7-2 and 8-2 show parts of the images that are captured, respectively, by the aforementioned two mutually adjacent sensors 8, 9 in the two moments of time. The enlarged view of FIG. 9 shows the first image portion captured by sensor 8, that corresponds to the right portion of the image of FIG. 7-2. Such first portion is identical to the first image portion captured by sensor 9 and corresponding to the left portion of the image of FIG. 8-2.

According to a variant embodiment of the invention, that will be disclosed more in detail in the following, the combination of the images from each pair of mutually adjacent sensors 8, 9 occurs without calculating the time interval between the two images, but rather by comparing the two images in order to find pairs of geometrical features 53 in common therein, from which geometrical transformations of the images are computed that allow to overlap the two geometrical features 53 of each pair.

Preferably, the length of each one of the aforementioned first portions 10a, 11a is comprised between 10 mm and 20 mm, in order to combine the opposite needs, on the one hand, to have a sufficient image overlap as to allow their comparison, and, on the other hand, to maximize the overall length of the field of view and, hence, the maximum width of the leather 50 that can be inspected.

As an example, in order to cover a maximum inspection width of 3050 mm, five sensors 8, 9 may be used, that are arranged mutually staggered so that the mutual overlap areas are about 12 mm long each.

Preferably, the processing device is configured to generate a digital map of the leather 50 based on the images captured by the sensors 8, 9. The digital map comprises one or more geometrical features 53 of the leather 50, among which are, in particular, the defects of the leather. The aforementioned geometrical features 53 may to further comprise other geometrical parameters, such as, for example, the area of the leather.

The aforementioned digital map can be stored on a memory device, together with a univocal identifier that put them in relation with the leather 50 in order to allow to use the map in subsequent operations to be performed on the leather.

Preferably, the digital map comprises a plurality of coordinates, that are representative of the aforementioned geometrical features 53 of the leather 50.

The aforementioned coordinates may be so configured as to provide a vector representation of one or more of the aforementioned geometrical features 53. More precisely, the aforementioned coordinates may identify a plurality of points belonging to a curve that delimits each geometrical feature 53. Advantageously, the aforementioned vector representation is suitable to be easily read and subsequently processed in case of need.

The aforementioned subsequent processing might be required, for example, in order to adapt the digital map to the actual state of the leather 50 just before performing any other process on the leather. For example, in case of a cut process aimed at obtaining portions of leather to be used in the manufacturing of finished products, it is necessary to define a usable area without defects.

To this end, it is to be reminded that, generally, the digital map is acquired by the tanner during, or at the end of, the treatment processing on the leather, while the subsequent processing of the leather often occurs at the final user, in times and locations that are different than those related to the generation of the digital map. As a consequence, in the subsequent processing, the leather may be in a condition that is different from that in which it was had during the inspection, for example due to shape settlements, different environmental conditions, elastic deformations, or, more simply, position change. Generally, the aforementioned different conditions result in corresponding changes in the geometry of the leather 50 compared to the moment when the digital map was generated.

Operatively and as shown in FIG. 1, the leather 50 is loaded on the first conveyor belt 12a of the inlet area 12 having the grain side facing upwards. From there, the leather proceeds to the stretching unit 14 for stretching possible wrinkles.

Afterwards, the leather is arranged in contact with the first area 3a of the first feeding roller 1 of the feeding unit 40 and is kept there thanks to the suction force of the depression generation device. The leather is then driven in succession to the stations 7a and 7b of the sensor unit 7 for capturing corresponding images of the outer side (grain side).

Once the leather reaches the second area 3b of the first roller 1, the pressure present there forces its separation from the cylindrical surface 3 and allows its conveyance towards the cylindrical surface 4 of the second feeding roller 2, where the leather is driven to the station 7c of the sensor unit 7 to capture the image of the rear side (flesh side).

As anticipated, the present invention also comprises an inspection method, referred to in the overall in FIG. 10 as 200, to detect the defects in a leather 50 by means of an inspecting machine 100 of the kind above disclosed.

For simplification purpose, reference will be made to the variant embodiment of an inspecting machine 100 shown in FIGS. 1-5, and, in particular, to the corresponding sensor unit 7, schematically shown in FIG. 11. The aforementioned sensor unit 7 comprises three stations 7a, 7b, 7c, each one of which comprises in turn five sensors 8, 9, only two of which, for simplification purpose, are indicated in the figure, for a total of 15 sensors. Two stations 7a e 7b capture the grain side, while station 7c captures the flesh side. The different stations 7a, 7b, 7c have similar configurations and arrangements for the corresponding sensors, so that the overall capture width be the same for all stations.

It is remarked that the configuration just disclosed is not limiting, and the invention is also applicable, in similar way, to variant embodiments in which the number of stations, their arrangement relative to the leather, and the number of sensors for each station, are different from the ones above disclosed, and/or in which the configuration, arrangement, and/or number of sensors, as well as the overall capture width, differ between the stations.

Figure 11:
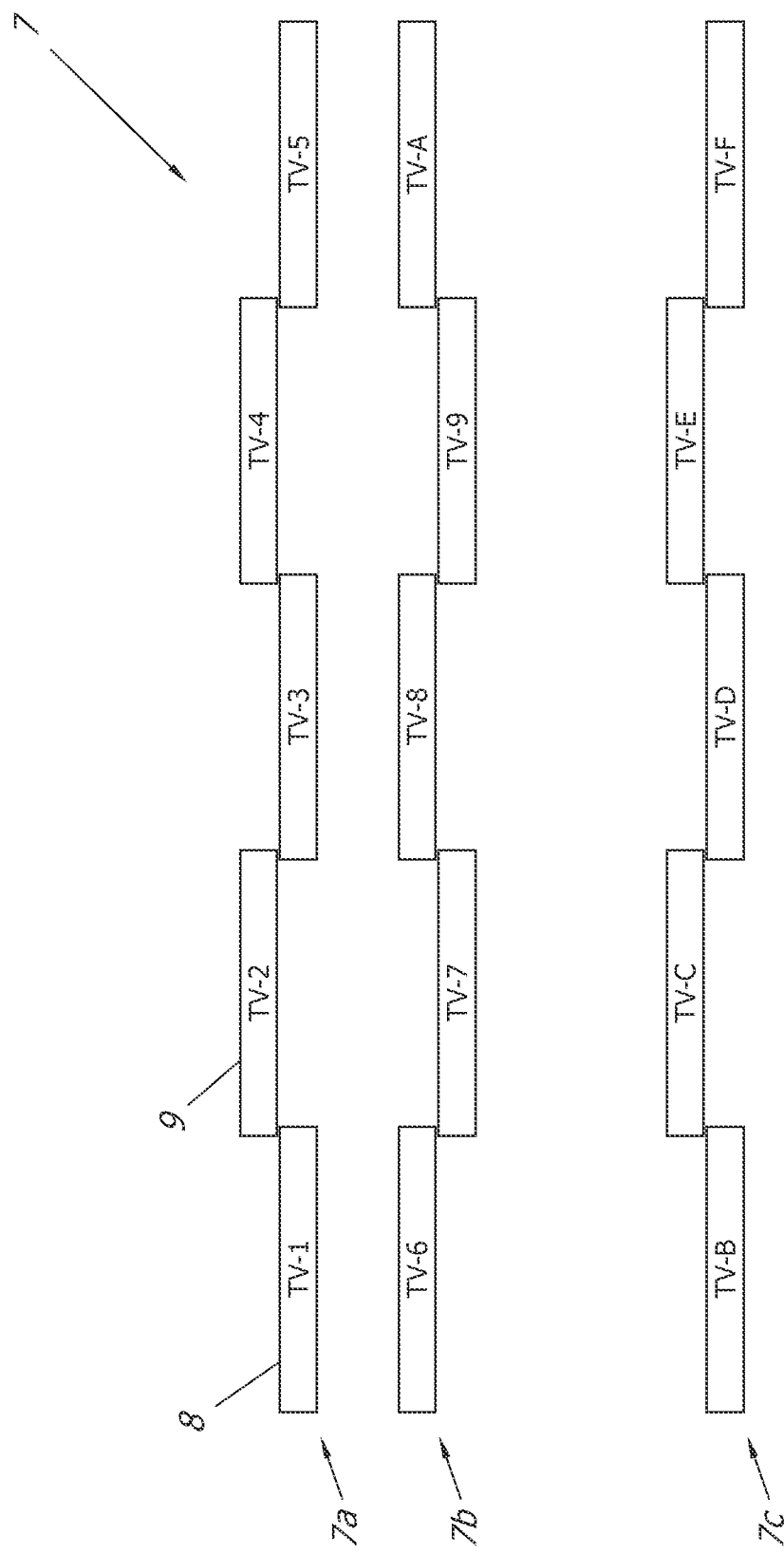
FIG. 11 shows the sensor unit of the inspecting machine of the invention, in schematic view.

For better precision, each sensor 8, 9 in FIG. 11 is identified with the label TV and with a corresponding hexadecimal digit from 1 to F. As a consequence, TV-1-TV-5 indicate the sensors in the first station 7a, TV-6-TV-A those in the second station 7b, TV-B-TV-F those in the third station 7c. Sensors TV-1, TV-3, TV-5 in the first station 7a are mutually aligned and correspond to the sensors more generally indicated as 8, while sensors TV-2 and TV-4, which are mutually aligned but, with respect to the previous ones, are offset in direction X and staggered in a direction perpendicular to direction X, correspond to the sensors more generally indicated as 9. A similar configuration can be observed for stations 7b and 7c.

First of all, the above method 200 envisages a step 201 of capturing an image 60 of the leather 50 by means of each one of the aforementioned image sensors TV-1-TV-F. In the following, the image captured by the generic sensor will be referred to as 60, while, to indicate the image by a specific sensor, the identifying digit of the sensor will be added as a subscript, hence obtaining $60_1$-$60_F$.

Figure 12:
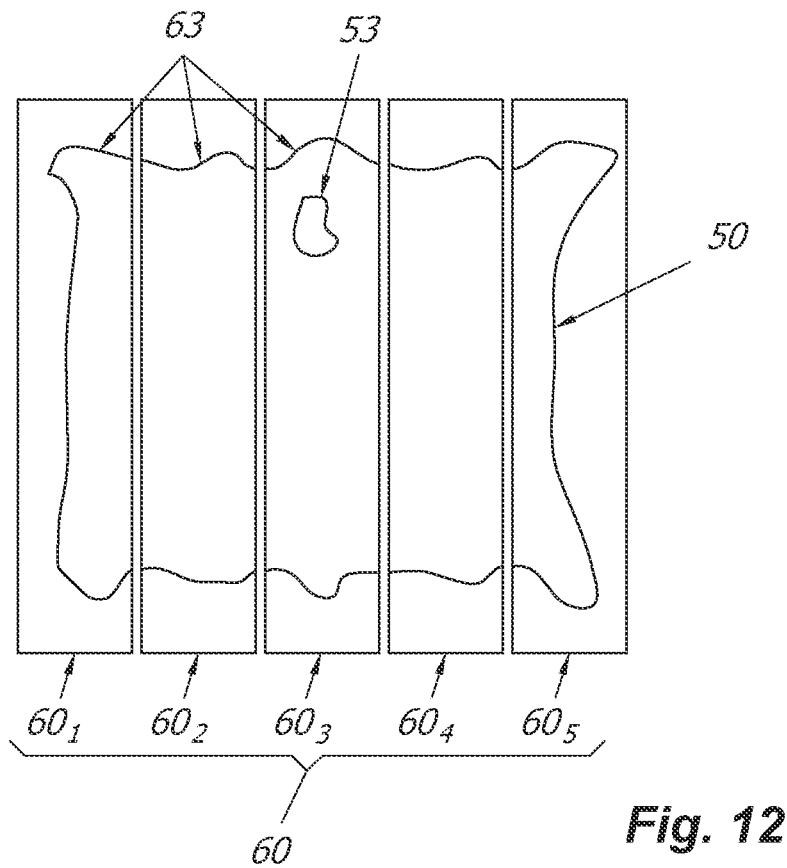

FIG. 12 shows the images $60_1$-$60_5$ of the leather 50 as captured by sensors TV-1-TV-5 in station 7a. Clearly, a similar configuration can be observed for the other stations as well.

Subsequently, the method 200 comprises a step 202 of detecting, in each image 60, the aforementioned geometrical features 53 of the leather 50. Some geometrical features 53 may not be captured by all stations, e.g. because they are visible only from one side of the leather 50, or only under the lighting of a specific station. For simplification purpose, FIGS. 12-16 show only one geometrical feature.

The method 200 further comprises a step 203 of defining a numerical representation 61 for each geometrical feature 53. By "numerical representation" it is meant, in general, a group of data that conventionally represent the geometrical feature 53.

In general, and as indicated in FIG. 10, each numerical representation 61 comprises one or more pairs of coordinates (x, y) relating to the corresponding geometrical feature 53, relative to the reference system of the image sensor TV-1-TV-F by which the geometrical feature was captured, and possibly one or more parameters W representative of corresponding geometrical aspects of the geometrical feature 53.

In case of an edge portion of the leather, the corresponding numerical representation 61 comprises an approximation of the profile 63 of the portion itself, indicated in FIG. 12. The aforementioned approximation can be expressed, e.g., through the coordinates (x, y) of several points of the profile, that then can be interpolated through a polygonal, a spline, or other entities.

In case of a geometrical feature 53 corresponding to a defect, the corresponding numerical representation 61 may comprise a plurality of coordinate pairs (x, y) defining the contour of the defect, similarly to what happens for the edges of the leather, while the above parameters W may comprise qualitative aspects, like kind of defect, extent, and so on, and/or quantitative aspects, like the area, the perimeter, and so on.

As previously mentioned, a geometrical feature 53 may also be a reference point, or "keypoint", namely a feature that is particularly distinguishable from the surface of the leather, even though it may not necessarily be a defect. For this kind of geometrical feature, the corresponding numerical representation 61 may comprise a single coordinate pair (x, y), that conventionally defines the position of the geometrical feature, while the parameters W, called in jargon "descriptors", are defined so as to conventionally define the aspect of the area around the above coordinate pair (x, y). Still preferably, the parameters W are defined so as to be invariant with respect to an affine transformation of the corresponding geometrical feature 53 on the plane of the leather 50. This brings an advantage that will be apparent hereinafter.

The above mentioned elements of the numerical representation 61 may be defined through per-se known algorithms such as, for example, ORB, BRISK, AKAZE, GFTT, FAST, AGAST, and so on.

Preferably, the reference points are identified by means of an algorithm that is distinct from, and independent of, the algorithm used for identifying the other geometrical features 53.

It may also happen that a reference point is identified in correspondence of a defect. In this case, it may occur that two mutually independent geometrical features 53 relating to the above defect are defined, that differ from the definition of the corresponding numerical representation 61: coordinates and descriptors of the reference point in the first instance, coordinates of the contour of the defect, plus possible parameters, in the second instance.

The method further comprises a step 204 of detecting each pair of numerical representations 61 that represent the same geometrical feature 53 captured by a corresponding pair of image sensors 8, 9 belonging to the same station 7a, 7b, 7c. Specifically, such an event may occur for each pair of image sensors 8, 9 in the same station whose fields of view 10, 11 overlap at corresponding first portions 10a, 11a, as in the case of FIGS. 7-1 and 8-1. For simplification, the two sensors of any one of the above pairs will be referred to in the following by the wording "adjacent sensors".

Therefore, in the step 204 just disclosed, those geometrical features 53 that are captured by both sensors of the pair at the first portions 10a, 11a are searched, so as to identify the corresponding pairs of numerical representations 61. Thus, both numerical representations of each one of the aforementioned pairs represent the same geometrical feature 53, as seen by the two sensors of a corresponding pair.

Preferably, the pairing of the numerical representations 61 is done based on the comparison of the corresponding parameters W. In fact, it is reminded that, in general, the same geometrical feature 53 captured by two adjacent sensors 8, 9 corresponds to two numerical representations 61 whose coordinates (x, y) are mutually different, due to the different positions of the two sensors 8, 9 and of their possible misalignment, as it will be explained in more detail shortly. On the contrary, at least a part of the parameters W of the two numerical representations are mutually equal, except for minor differences. In particular, this applies to the reference points previously defined, due to the invariance of the corresponding descriptors with respect to an affine transformation. Therefore, these points are particularly suited to be used for performing the above pairing.

More in detail, each geometrical feature 53 included in the overlap area between two adjacent sensors 8, 9 is detected by both sensors, and for it, two corresponding and distinct numerical representations 61 are defined.

However, in general, due to the different positions of the two sensors and to possible aligning defects, both on the plane parallel to the leather 50, and in that perpendicular thereof, the coordinates (x, y) belonging to the aforementioned two numerical representations corresponding to a given geometrical feature 53 are mutually different.

On the contrary, where the reference points are concerned, the corresponding descriptors are generally identical, or at least similar, in particular as concerns the geometrical aspects that are invariant, within the meaning previously defined. Therefore, it is understood that the comparison between the descriptors allows to detect, simply and reliably, that pair of numerical representations 61, corresponding to the two sensors 8, 9, that corresponds to the same geometrical feature 53.

The identification of the above pairs of numerical representations 61 is done for each station 7a, 7b, 7c.

Afterwards, a step 205 is performed in order to define, for each pair of adjacent sensors 8, 9 belonging to the same station 7a, 7b, 7c, a corresponding affine transformation Tij that transforms the coordinates $(x_i, y_i)$ of the numerical representations 61 of the aforementioned pairs, relating to the sensor i-th, in the coordinates $(x_j, y_j)$ of the corresponding numerical representations 61, relating to the sensor j-th, namely $$(x_j, y_j) = Tij(x_i, y_i) \quad (1)$$

The above indices i and j generally identify the two sensors of the pair, according to the hexadecimal notation previously defined. Therefore, for example, the affine transformation that transforms the coordinates of a geometrical feature 53 relating to sensor TV-1 in those relating to sensor TV-2 will be indicated by T12, while the one between sensors TV-9 and TV-A will be indicated by T9A, and so on.

As known, an affine transformation is a transformation preserving parallelism between lines, but not necessarily distances and angles.

Advantageously, the aforementioned affine transformation Tij allows to take into account the deformations on the images 60 resulting from possible misalignment between the two adjacent image sensors 8, 9. This is possible because the image deformation due to misalignment of a linear-telecentric optics, as those in CIS sensors are, can be defined, at least as a first approximation, in terms of an affine transformation. Moreover, an affine transformation can also take into account small deformations that the leather 50 could undergo while passing between one sensor and the other.

In order to take into account greater deformations of the leather 50, that cant' be expressed through an affine transformation, each affine transformation Tij may be defined by using a criteria that minimizes the difference between the coordinates obtained by the image captured from the second sensor and those obtained through the transformation of the coordinates obtained through the image captured by the first sensor, according to per-se known algorithms.

After defining the aforementioned affine transformations Tij, they are used in a further method step 206 for transforming the coordinates (x, y) belonging to one or more of the numerical representations 61 captured by the sensors of any given station 7a, 7b, 7c in the corresponding transformed coordinates (x*, y*) relative to a common reference system for that station. The aforementioned common reference system may be that of a reference sensor of the same station, e.g. the middle sensor. Clearly, in order to transform the coordinates (x, y) relative to a sensor not adjacent to the reference sensor, it is necessary to use the product of the affine transformations corresponding to each pair of adjacent sensors comprised between the aforementioned sensor and the reference sensor.

The above operation 205 is applied at least to the geometrical features 53 corresponding to the defects and to the leather edges.

Figure 13:
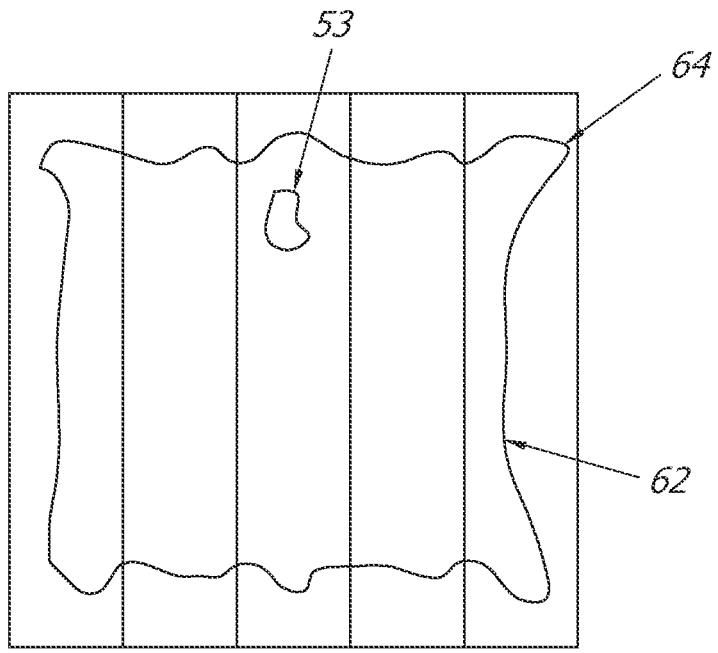

The execution of the above steps allows to define a digital map 62 of the leather 50 for each station 7a, 7b, 7c, as the one shown in FIG. 13. The aforementioned digital map 62 comprises the numerical representations 61 of the said geometrical features 53 relative to the aforementioned common reference system.

For each pair of adjacent sensors 8, 9, several affine transformations Tij for different areas of the leather 50 may also be defined. This allows to take into account localized deformation of the leather 50, thus obtaining a more precise transformation of the coordinates. A specific algorithm calculates all the affine transformations Tij needed for each pair of adjacent sensors, as well as the contours of the areas in which each affine transformation is applicable.

Clearly, what has been previously disclosed is also applicable in a similar way to the case just disclosed, except for the geometrical features 53 located outside of the aforementioned areas. If k is the number of affine transformations Tij for a given pair of sensors, the transformed coordinates (x*, y*) of a point with coordinates (x, y) may be defined by applying each one of the k affine transformations Tij to the coordinates (x, y) and then calculating the weighted average of the resulting coordinates, the weights being related to the inverse of the distance $D_k$ of the point (x, y) from the corresponding areas, in particular from their contours. A known method for calculating the aforementioned weighted average is, for example, the Shepard's method.

It is understood that the aforementioned weighted average based on the inverse of the distance allows to attribute, in calculating the transformed coordinates, bigger influence to the transformations that correspond to the areas that are closer to the geometrical feature 53 in question with respect to the farther ones.

As previously said, the geometrical features 53 also comprise the edge portions of the leather 50 captured by each image sensor 8, 9, and the numerical representation 61 of each edge portion is such as to allow recreating the profile 63 of the edge portion, or of an approximation thereof, in the form of a continue curve, that may be a polygonal, a spline, etcetera.

The profiles 63 of the aforementioned edge portions, once subjected to the aforementioned affine transformations Tij, may determine an overall profile that is discontinuous, for example due to localized deformations of the leather.

In order to correct the aforementioned discontinuities, the method preferably comprises a step 207 of correcting the affine transformations Tij based on the aforementioned profiles 63 of the edge portions. More in detail, the aforementioned correction step 207 is performed in such a way that the profiles 63 of the edge portions, as a consequence of the application of the corrected affine transformations Tij, form a continue edge profile 64. FIG. 13 shows the result achieved after the aforementioned correction step 207.

The calculation of the transformed coordinates (x*, y*) in the common reference system is done based on the affine transformations Tij as above corrected, to the advantage of a higher precision of the digital map 62 so obtained.

It is noticed that the correction of the aforementioned affine transformations Tij may me done, from the operative point of view, either by modifying the corresponding transformation matrixes as previously calculated, or by defining new corrected transformation matrixes that are applied in place of the original ones. In the present description, the aforementioned two variants are considered to be equivalent and the reference Tij is used in both cases to indicate the affine transformations used to calculate the transformed coordinates (x*, y*).

The method disclosed so fa allows to obtain a digital map 62 of the leather 50 for each station 7a, 7b, 7c of the sensor unit 7. In FIGS. 14-1, 14-2 and 14-3, the three digital maps corresponding to the three stations are indicated, respectively, by 62a, 62b and 62c. Nevertheless, in general, the three digital maps 62 do not perfectly overlap, either because of the misalignment between the sensors belonging to the different stations, or because of the difference between the images as captured by different stations, or, for example, because of deformations of the leather between two stations, of different capturing conditions, etcetera. That situation is schematically shown in FIG. 15, where the differences between the three maps exaggerated in order to allow distinguishing them.

Preferably, in order to improve the matching between the aforementioned digital maps 62, the method 200 envisages the further step 208 of defining a rigid transformation Rij that transforms the continuous edge profile 64 of the digital map corresponding to each station 7a, 7b, 7c in such a way as to minimize the deviations with respect to the continuous edge profile 64 of the digital map corresponding to a given one of the aforementioned stations 7a, 7b, 7c, taken as reference. In the used notation, the first index i represents the sensor that defines the common reference system of the station under examination, while the second index j represents the sensor that defines the common reference system of the reference station.

For exemplary purpose, the figures show as reference sensors those in the middle of each station, i.e. sensors TV-3, TV-8 and TV-D, and as reference station the station 7a, whose map 61a is shown in FIGS. 14-16 with a thicker edge, in order to facilitate distinguishing it. On the contrary, the two maps 61b and 61c of stations 7b and 7c are represented by, respectively, dashed lines and dot-dash lines.

In the exemplary situation just disclosed, the aforementioned step 208 generates two rigid transformations R83 and RD3 that transform, respectively, the two maps 61b and 61c in order to express them in the reference system of station 7a.

The aforementioned rigid transformations R83 and RD3 are applied to the transformed coordinates (x*, y*) of the digital maps 62b and 62c corresponding to stations 7b and 7c, in order that they better match with the digital map 62a corresponding to the reference station 7a. The result of the aforementioned step is shown in FIG. 16. The result is an overall digital map 62 grouping the data of all stations.

Preferably, the method 200 comprises a further step of improving the digital maps 62 obtained through the aforementioned rigid transformations Rij based on one or more geometrical features 53 that are in common among the corresponding digital maps 62.

The aforementioned improving operation comprises a step 209 for identifying, from the digital map 62 corresponding to a first station 7a, 7b, or 7c, e.g. station 7a, the geometrical features 53 that are susceptible to be detected by a second station, for example one of the stations 7b, 7c.

The identification of the aforementioned common geometrical features 53 may be done, for example, based on the corresponding parameters W. For example, some kinds of defects may extend on both sides of the leather 50 and, thus, they may be detected both by a station that captures the grain side, and from a station that captures the flesh side.

Once identified the aforementioned common geometrical features 53, a further step 210 is performed for detecting the corresponding numerical representations 61 in the digital map 62 corresponding to the second station 7b or 7c.

In a subsequent step 211, the affine transformations Tij corresponding to the second station are corrected in order that the transformed coordinates (x*, y*) of the numerical representations 61 identified in the previous step, further transformed by applying the corresponding rigid transformation Rij above disclosed, coincide with those of the numerical representations 61 of the same geometrical features 53 in the digital map 62 corresponding to the first station 7a, or present the minimum deviation thereof.

The latter correction allows to further increase the matching between the different digital maps 62, thus achieving an optimal description of the leather 50.

From what has been disclosed above, it is understood that the inspecting machine and the method of inspection of the invention achieve the preset aims.

In summary, it is understood that the method as disclosed so far takes advantage of the geometrical features 53 detected in the overlapping areas, particularly the reference points, to define the affine transformations Tij that allow to express all other geometrical features 53, particularly defects and leather edges, in relation to a common reference system for each station 7a, 7b, 7c, so as to obtain corresponding digital maps 62. That operation corresponds to combining the images obtained from the different image sensors 8, 9 of the station.

Moreover, the method uses special geometrical features of the maps 62, in particular leather edges and defects, for correcting and improving the above mentioned affine transformations Tij, as well as to overlapping the maps.

Where the technical elements specified in the claims are followed by reference signs, those reference signs are included to the sole aim of improving the understanding of the invention and, hence they do not imply any limitation of the claimed scope of protection.

The invention claimed is:

1. An inspecting machine (100) for leathers (50), comprising:
 a feeding unit (40) for a movement of a leather (50) according to an advancement direction (X);
 a sensor unit (7) configured to capture images of said leather (50) during said movement; and a processing device configured to identify one or more geometrical features (53) of said leather (50) based on an analysis of said images;

wherein said sensor unit (7) comprises a plurality of contact image sensors (8, 9) faced to said leather (50) when said leather (50) is moved by said feeding unit (40), said contact image sensors (8, 9) being arranged crosswise to said advancement direction (X); and wherein said sensor unit (7) comprises said plurality of said contact image sensors (8, 9) arranged in mutually different positions according to said advancement direction (X) and mutually staggered according to a direction perpendicular to said advancement direction (X) in such a way that respective optical fields (10, 11) have corresponding first sections (10*a*, 11*a*) that are mutually superposed according to said advancement direction (X) to capture corresponding first image portions of a same first portion (54) of said leather (50) in two corresponding mutually different moments, and corresponding remaining sections (10*b*, 11*b*) to capture second image portions of other two respective mutually different portions (55, 56) of said leather (50) that are adjacent to said first portion (54), said processing device being configured to combine the images captured by said contact image sensors (8, 9) based on the analysis of said first image portions.

2. The inspecting machine (100) according to claim 1, wherein said processing device is configured to determine a time interval between said two corresponding mutually different moments in order to being able to synchronize said images.

3. The inspecting machine (100) according to claim 1, wherein said processing device is configured to produce a digital map (62) of said leather (50) comprising said one or more geometrical features (53) of said leather (50).

4. The inspecting machine (100) according to claim 1, wherein said feeding unit (40) comprises:
one or more movable surfaces (3, 4) that can be positioned in contact with said leather (50), each of said one or more movable surfaces (3, 4) comprising a plurality of holes (5);
motorization means (15, 16) for a movement of each one of said one or more movable surfaces (3, 4) according to said advancement direction (X); and
a depression generation device connectable to one or more holes of said plurality of holes (5) to generate a depression sufficient to keep a portion (51, 52) of said leather (50) adhering to said one or more movable surfaces (3, 4) during said movement, so as to cause said leather (50) to advance according to said advancement direction (X).

5. The inspecting machine (100) according to claim 4, wherein each movable surface (3, 4) defines a plurality of grooves (17), and wherein said holes (5) are defined a level of said grooves (17) in such a way that said holes result, wholly or partially, lowered with respect of said movable surface (3, 4).

6. The inspecting machine (100) according to claim 4, further comprising a sealing unit (6) operatively associated with each one of said one or more movable surfaces (3, 4) and configured to limit a transmission of said depression generated by said depression generation device only to a first group of holes (5*a*, 5*b*) of said plurality of holes (5) that are comprised within a first area (3*a*, 4*a*) of said movable surface (3, 4), hence preventing said transmission from occurring to remaining holes of said plurality of holes (5).

7. The inspecting machine (100) according to claim 6, further comprising a pressure generation device connectable to one or more holes of said plurality of holes (5) to generate a thrust in correspondence with at least a second area (3*b*, 4*b*) of said movable surface (3, 4) that is arranged downstream of said first area (3*a*, 4*a*) according to said advancement direction (X), said thrust being sufficient to force a detachment of said leather (50) from said movable surface (3, 4).

8. The inspecting machine (100) according to claim 4, wherein said one or more movable surfaces (3, 4) comprise two of said movable surfaces (3, 4), said feeding unit (40) being configured to put the two mutually opposite faces of said leather (50) in contact with, respectively, said two movable surfaces (3, 4) in succession.

9. The inspecting machine (100) according to claim 4, wherein each one of said movable surfaces (3, 4) is a cylindrical surface belonging to a corresponding feeding roller (1, 2) that defines a respective longitudinal axis (Y1, Y2) perpendicular to said advancement direction (X) and around which said feeding roller (1, 2) is rotatably mounted for a rotation according to a corresponding direction of rotation (Z1, Z2).

10. The inspecting machine (100) according to claim 9, wherein said inspecting machine comprises two feeding rollers (1, 2), said motorization means (15, 16) being configured to define, for said two feeding rollers (1, 2), two corresponding mutually opposite directions of rotation (Z1, Z2).

11. The inspecting machine (100) according to claim 1, wherein said sensor unit (7) comprises a plurality of stations (7*a*, 7*b*, 7*c*), arranged in corresponding mutually different positions along said advancement direction (X), each station (7*a*, 7*b*, 7*c*) comprising said plurality of said contact image sensors (8, 9) arranged in said mutually different positions according to said advancement direction (X) and mutually staggered according to said direction perpendicular to said advancement direction (X) in such a way that the respective fields of view (10, 11) have the corresponding first portions (10*a*, 11*a*) that mutually overlap according to said advancement direction (X).

12. A method (200) for inspecting a leather (50) in an inspecting machine (100) comprising the following steps:
capturing (201) an image (60) of said leather (50) using each one of said contact image sensors (8, 9);
in each one of said images, identifying (202) a corresponding plurality of said geometrical features (53) of said leather (50);
defining (203) a numerical representation (61) for each geometrical feature (53), said numerical representation (61) comprising at least one pair of coordinates (x, y) of said geometrical feature (53), relative to a reference system of a corresponding contact image sensor (8, 9);
for each pair of contact image sensors (8, 9) whose fields of view (10, 11) have mutually overlapping first portions (10*a*, 11*a*), identifying (204) each pair of numerical representations (61) corresponding to a same geometrical feature (53) captured in said first portions (10*a*, 11*a*) by the contact image sensors (8, 9) of said pair;
for each one of said pairs of contact image sensors (8, 9), defining (205) an affine transformation (Tij) that transforms the coordinates (x, y) of the numerical representations (61) relating to a first sensor (8, 9) of said pair of sensors and that belongs to one of said pairs of numerical representations (61) in the coordinates (x, y) of the corresponding numerical representations (61) relating to a second sensor (8, 9) of said pair of sensors, or that minimizes a difference therebetween; and for each one of the coordinates (x, y) of one or more of said numerical representations (61), calculating (206) corresponding transformed coordinates (x*, y*) relative to a common reference system by applying said affine transformations (Tij), in order to obtain a digital map (62) of said leather (50).

13. The method (200) according to claim 12, wherein said geometrical features (53) comprise each of edge portions of said leather (50) captured by the corresponding said image sensors (8, 9), each numerical representation (61) of said edge portions being adapted to define profiles (63) of the corresponding edge portions, said step of calculating (206) said corresponding transformed coordinates (x*, y*) comprising a step of correcting (207) each affine transformation (Tij) in such a way that said profiles (63) of said edge portions, as a consequence of an application of said corrected affine transformations (Tij), form a continuous edge profile (64).

14. The method (200) according to claim 13, further comprising the following steps:

for each one of said stations (7a, 7b, 7c), executing the method (200) according to claim 13 in order to obtain a corresponding digital map (62) of said leather (50); and defining a rigid transformation (208) that transforms said continuous edge profile (64) in the corresponding digital map (62) corresponding to each one of said stations (7a, 7b, 7c) in such a way as to minimize deviations with respect to the continuous edge profile (64) of the digital map (62) relating to a reference station among said stations (7a, 7b, 7c).

15. The method (200) according to claim 14, further comprising the following steps:

from the digital map (62) corresponding to a first one of said stations (7a, 7b, 7c), identifying (209) one or more geometrical features (53) susceptible of being detected by a second one of said stations (7a, 7b, 7c);

in the digital map (62) corresponding to said second station (7a, 7b, 7c), identifying (210) the numerical representations (61) corresponding to said one or more geometrical features (53); and correcting (211) said affine transformations (Tij) corresponding to said second station (7a, 7b, 7c) in such a way that said transformed coordinates (x*, y*) corresponding to said identified numerical representations (61), further transformed by said rigid transformation, coincide with transformed coordinates corresponding to the numerical representations (61) of said one or more geometrical features (53) in the digital map (62) corresponding to said first station (7a, 7b, 7c), or has a minimum deviation.

* * * * *